United States Patent [19]

Mizuno et al.

[11] Patent Number: 5,210,271

[45] Date of Patent: May 11, 1993

[54] INTERMEDIATES FOR THE PRODUCTION OF DIETHANOLAMINE

[75] Inventors: Yukio Mizuno, Toyono; Miichiro Arita, Nara, both of Japan

[73] Assignee: Takeda Chemical Industries, Ltd., Osaka, Japan

[21] Appl. No.: 748,964

[22] Filed: Aug. 23, 1991

[30] Foreign Application Priority Data

Sep. 3, 1990 [JP] Japan .................... 2-234302

[51] Int. Cl.$^5$ .............. C07C 255/25; C07C 253/04; C07C 271/10; C07C 269/02
[52] U.S. Cl. .................... 558/442; 558/452; 558/451
[58] Field of Search ............. 558/442, 452

[56] References Cited

U.S. PATENT DOCUMENTS

| 1,972,465 | 9/1934 | Ulrich et al. | 558/452 |
| 3,465,036 | 9/1969 | Dundon | 558/442 X |
| 4,987,130 | 1/1991 | Tsushima, I et al. | 514/210 |

FOREIGN PATENT DOCUMENTS

| 0278621 | 8/1988 | European Pat. Off. | 558/442 |
| 564787 | 11/1932 | Fed. Rep. of Germany | 558/452 |

*Primary Examiner*—Floyd D. Higel
*Attorney, Agent, or Firm*—Wegner, Cantor, Mueller & Player

[57] ABSTRACT

A method of producing diethanolamine derivatives or acid salts thereof according to the reaction scheme:

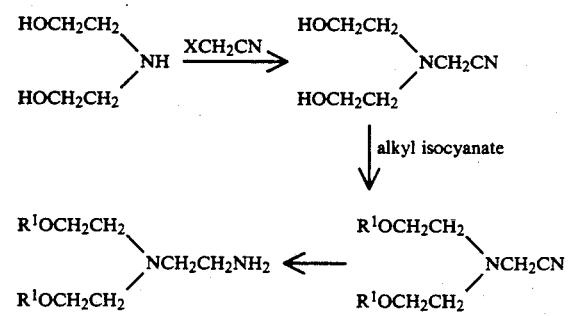

wherein X stands for a leaving group; and $R^1$ stands for an alkylcarbamoyl group, which provides an industrially advantageous method of preparing the subject matter useful as an antiarrhythmic agent.

2 Claims, No Drawings

INTERMEDIATES FOR THE PRODUCTION OF DIETHANOLAMINE

This invention relates to a method of preparing diethanolamine derivatives useful as antiarrhythmic agents and to new intermediates employed in the method. More specifically, the present invention relates to an industrially advantageous method of preparing a diethanolamine derivative of the formula,

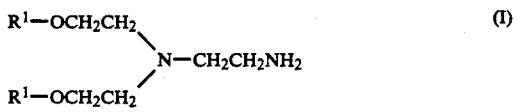

wherein R¹ stands for alkyl carbamoyl group, and an acid addition salt thereof, and to diethanolamine derivatives, which are useful novel intermediates in the above method, of the formula;

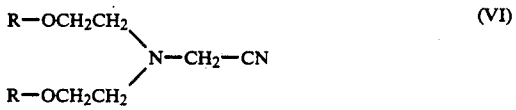

wherein R stands for hydrogen or alkyl carbamoyl group.

Arrhythmia is one of the diseases often observed especially in old people, and when it takes a serious turn, the patient's life becomes in danger. Recently, coronary diseases have been rapidly increasing, and a serious concern is directed to counter-measures to fatal arrhythmia brought on by those diseases.

As antiarrhythmic agents, various pharmaceutical products have been developed and used clinically. However, among those agents, since differences in effectiveness are observed depending on conditions of diseases due to complicated causes of arrhythmia, antiarrhythmic agents effective for broadened types of arrhythmia and with less side effects have been sought for.

As a part of these research works, diethanolamine derivatives (I) having a unique structure and their acid addition salts were found and reported [U.S. Pat. No. 4,987,130].

The compound (I), having symmetric structure relative to the nitrogen atom of the tertiary amine, can be synthesized by N-alkylation of diethanolamine and carbamoylation of two hydroxyl groups. In the specification of U.S. Pat. No. 4,987,130, therefore, there is disclosed a method of producing diethanolamine derivatives (I), which comprises protecting the secondary amino group with t-butyloxycarbonyl group (Boc group) to distinguish essentially two reaction points of diethanolamine, i.e. the secondary amino group and the two hydroxyl groups, from each other, carbamoylating the two hydroxyl groups, then removing the Boc group, introducing a phthalimido alkyl chain by N-alkylation, and then removing the phthaloyl group.

This method can be hardly considered industrially advantageous for the synthesis of diethanolamine derivatives (I), because both the Boc group and the phthaloyl group employed as protecting groups of the secondary amino group and the primary amino group are expensive and, besides, the number of reaction steps is relatively greater, since they include protecting and deprotecting reactions.

The present invention relates to an industrially advantageous method of preparing diethanolamine derivatives (I) or an acid salt thereof which is useful as an antiarrhythmic agent, without any step for introducing and removing protecting groups and having a smaller number of reaction steps than prior methods, and diethanolamine derivatives (VI) to be employed as useful novel intermediates in the above method.

The present invention provides (1) a method of preparing a diethanolamine derivative (I) or an acid addition salt thereof, which is characterized by subjecting a compound (V) of the formula,

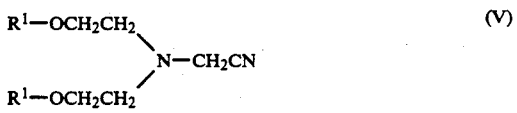

wherein R¹ stands for alkylcarbamoyl group, to catalytic reduction, (2) a method of preparing a diethanolamine derivative (I) or an acid addition salt thereof, which is characterized by allowing a compound of the formula,

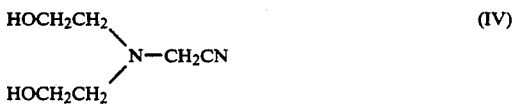

to react with alkyl isocyanate, then subjecting the resultant compound (V) to catalytic reduction, (3) a method of preparing a diethanolamine derivative (I) or an acid addition salt thereof, which is characterized by allowing diethanolamine of the formula,

to react with an acetonitrile derivative (III) of the formula,

wherein X stands for a leaving group, then allowing the resultant compound (IV) to react with alkyl isocyanate, then subjecting the resultant compound (V) to catalytic reduction, and (4) the compounds (IV) and (V).

Examples of the alkyl carbamoyl group shown by R' and R include lower alkyl carbamoyl groups having about 1 to 6 carbon number at its alkyl moiety such as methylcarbamoyl, ethylcarbamoyl, n-propylcarbamoyl, isopropylcarbamoyl, n-butylcarbamoyl, isobutylcarbamoyl, sec-butylcarbamoyl, tert-butylcarbamoyl, n-pentylcarbamoyl, isopentylcarbamoyl, neopentylcarbamoyl, tert-pentylcarbamoyl, n-hexylcarbamoyl, isohexylcarbamoyl, neohexylcarbamoyl and tert-hexylcarbamoyl, and among them, the n-butyl carbamoyl group is preferable.

Examples of leaving groups shown by X include halogen such as fluoro, chloro, bromo and iodo, and a lower 1-4C alkoxy group such as methoxy, ethoxy, propoxy, isopropoxy, butoxy, isobutoxy, sec-butoxy, tert-butoxyl, and halogen is preferable, especially chloro and bromo are preferable.

As alkyl isocyanate, mention is made of a lower alkyl isocyanate having about 1 to 6 carbon number at its alkyl moiety such as methyl isocyanate, ethyl isocyanate, n-propyl isocyanate, isopropyl isocyanate, n-butyl isocyanate, isobutyl isocyanate, sec-butyl isocyanate, tert-butyl isocyanate, n-pentyl isocyanate, isopentyl isocyanate, neopentyl isocyanate, tert-pentyl isocyanate, n-hexyl isocyanate, isohexyl isocyanate, neohexyl isocyanate and tert-hexyl isocyanate.

As the acid addition salts of diethanolamine derivatives (I), mention is made of pharmacologically acceptable inorganic acid salts such as hydrochloride salts, sulfuric acid salts, nitric acid salts and phosphate and organic acid salts such as carbonate, sulfonate and sulfinate, and, among them, hydrochloride salts (dihydrochloride salts) are preferable.

In the following, the method of this invention is described in detail.

First, by allowing diethanolamine (II) to react with a compound represented by the formula (III), the compound (IV) is produced.

Diethanolamine (II) has two reaction points, i.e. the secondary amino group and two hydroxyl groups, and it has been known that the former is more potent in nucleophilic property than the latter.

This reaction is usually conducted in the presence of an acid acceptor. And, examples of an acid acceptor include tertiary amines such as triethylamine, N,N-diisopropylethylamine, tri-n-propylamine, tri-n-butylamine, etc., an aromatic amine such as pyridine, an inorganic base such as ammonia water, sodium hydroxide, sodium bicarbonate, sodium carbonate, etc. or a base such as a basic ion-exchange resin. The reaction may usually be conducted in a solvent. And, examples of the solvent include aliphatic hydrocarbon halogenides such as dichloromethane, dichloroethane, chloroform, etc., alcohols such as methanol, ethanol, etc., ethers such as dioxane, tetrahydrofuran, and, besides, acetone, acetonitrile, N,N-dimethylformamide, etc., and among them use of acetonitrile is most desirable. An acid acceptor is used at a ratio of 1 to 10 mols., desirably 2 or 3 mols. relative to one mole of a diethanolamine (II). An acid acceptor may be dissolved in a solvent before the reaction. An acetonitrile derivative (III) is used at a ratio of 1 to 5 mols., desirably 1 to 3 mols. relative to one mole of (II). The reaction temperature is usually at −70° to 100° C., desirably 0° to 80° C. The reaction time is usually 1 to 24 hours, desirably 1 to 5 hours. The reaction may for example be conducted by adding an acetonitrile derivative (III) dropwise at a ratio of 1 to 5 mols., desirably 1 to 3 mols. relative to one mole of (II), at −50° to 80° C., desirably 0° to 30° C., and then heating for 1 to 5 hours at 30° to 80° C., desirable 30° to 50° C.

While the reaction mixture can be subjected to the subsequent reaction after processing by a conventional manner such as filtration and concentration, then isolating and refining the compound (IV) by means of an alumina column chromatography, the reaction can be allowed to proceed in a one-pot reaction by adding alkyl isocyanate continuously without isolating the compound (IV).

On the other hand, there is a method which comprises using diethanolamine (II) as reaction substrate, solvent and acid acceptor. In this case, the reaction is conducted by using diethanolamine (II) at a ratio of 2 to 10g, desirably 2 or 3g relative to 1 g of the acetonitrile derivative (III). The reaction temperature is usually at −70° to 100° C., desirably 0° to 80° C. The reaction time is usually 1 to 24 hours, desirably 1 to 5 hours. For example, the reaction may be conducted by adding (III) to (II) dropwise at a temperature range between −50° to 80° C., desirably 0° to 50° C., and then heating for 1 to 5 hours at 30° to 80° C., desirable 30° to 50° C. Compound (IV) can also be isolated by extraction by adding to the resultant reaction mixture an aliphatic hydrocarbon halogenide such as dichloromethane, dichloroethane, chloroform, etc. or an ether such as dioxane, tetrahydrofuran, etc.

The reaction for obtaining the compound (V) from the compound (IV) and alkyl isocyanate is conducted by using a solvent other than alcohols, for example an aliphatic hydrocarbon halogenide such as dichloromethane, dichloroethane, chloroform, etc., ethers such as dioxane, tetrahydrofuran, etc., and any other suitable solvent such as acetone, acetonitrile, N,N-dimethylformamide, etc., or, depending on cases, the reaction is conducted in the absence of solvent. Usually, reaction between alcohols and isocyanates does not require the presence of a base, but the present reaction can be allowed to proceed advantageously by adding to the reaction system a catalytic amount or a not less than the stoichiometric amount of a tertiary amine such as triethylamine, N,N-diisopropylethylamine, tri-n-propylamine, tri-n-butylamine, etc., an aromatic amine such as pyridine, etc., an inorganic base such as ammonia water, sodium hydroxide, sodium bicarbonate, sodium carbonate, etc., or a base such as a basic ion-exchange resin. In the present reaction, since the compound (IV) reacts with alkyl isocyanate slowly, addition of a suitable amount of an appropriate base is preferable. The reaction temperature is usually at −70° to 100° C., desirably 0° to 80° C. The reaction time is usually 1 to 24 hours, desirably 1 to 5 hours. The reaction can be conducted for 1 to 50 hours at temperatures ranging from 0° to 60° C., desirably 30° to 50° C., after adding to the mixture of compound (IV) and the base dropwise alkyl isocyanate at a ratio of 2-5 mols, desirable 2-2.5 mols to one mole of compound (IV) at temperatures ranging from −20° to 80° C., desirably 0° to 50° C. While the compound (V) can be isolated by processing the reaction mixture in a conventional manner such as separation, it can be refined, when necessary, by means of an alumina column chromatography or a silica gel column chromatography. The next reaction can be allowed to proceed continuously with the reaction mixture of the compound (V).

The compound (I) is produced by subjecting the compound (V) to catalytic reduction. The catalytic reduction can be conducted in a conventional manner.

As methods of reducing nitrile to amine, there have been known a method using lithium aluminum hydride (J. Am. Chem. Soc., 73, 242 (1951)), catalytic reduction using Raney nickel (J. Am. Chem. Soc., 66, 876 (1944)), and electrolytic reduction (U.S. Pat No. 4,256,550) and diborane reduction, among others. For the reduction of compound (V) to compound (I), catalytic reduction is employed advantageously.

As the solvent for catalytic reduction, use is made of lower(1-4C) alcohols such as methanol, ethanol, propanol, etc., ethers such as dioxane, tetrahydrofuran, etc., aromatic hydrocarbon such as benzene, toluene, xylene, etc., ethyl acetate, acetic acid, N,N-dimethylformamide, etc. or a mixture of them, desirably, a mixture of lower(1-4C) alcohols and aromatic hydrocarbon. As the catalyst, while use is made of Raney nickel or Raney cobalt, modified Raney nickel or modified Raney cobalt can also be employed. The modified Raney nickel or modified Raney cobalt is prepared by, for example, the following method. A Raney nickel or Raney cobalt alloy prepared by adding to nickel or cobalt a metal such as iron, chromium, lead, manganese, etc. in an amount of about 0.01-3% in terms of atomic ratio relative to the nickel or cobalt is developed with potassium hydroxide or sodium hydroxide. The amount of the catalyst ranges from about 0.5 to 60 weight % relative to compound (V), desirably 10 to 40 weight %.

In this reaction, besides the catalyst, hydroxide or alcoholate of an alkali metal or alkaline earth metal is preferably added to the reaction system. As the hydroxide, mention is made of an alkali metal hydroxide such as sodium hydroxide, potassium hydroxide, lithium hydroxide, etc. and an alkaline earth metal hydroxide such as calcium hydroxide, barium hydroxide, magnesium hydroxide, etc. The amount of the hydroxide to be added to the reaction system ranges from about 50 to 1000 mg equivalent, preferably 100 to 500 mg equivalent, as the metal relative to 100 g of compound (V). The hydrogen pressure for the hydrogenation of the nitrile is normal or an elevated pressure in general, which ranges preferably from about 2 to 150 kg/cm$^2$ when the reaction is conducted on an industrial scale. No particular temperature range is required for the reaction in general, so long as the reaction is conducted at about 20° C. or higher, but preferably 30° to 150° C., especially 50° to 100° C. The reaction time varies with the amount of catalyst, hydrogen pressure and reaction temperature and ranges from about 1 to 10 hours.

The compound (I) thus obtained can be easily isolated and purified by a known means of separation and purification such as separation and silica gel column chromatography. An acid salt of the compound (I) can be prepared by adding an acid to the compound (I). As the acid, mention is made of inorganic acid such as hydrochloride, sulfuric acid, nitric acid, and phosphoric acid and organic acid such as carbonic acid, sulfonic acid and sulfinic acid. For example, by adding ethanolic or isopropanolic hydrogen chloride to the compound (I), hydrochloride salts (dihydrochloride salts) of the compound (I) can be obtained as crystals of high quality.

The compound (I) and an acid salt thereof which are prepared by the present invention, are used for a mammal including human as antiarrhythmic agents. The compounds (I) or their salts can be safety administered orally or parenterally, as such or after being processed into such dosage forms as powder, granule, tablet, capsule, suppository and injectable solution by means of the conventional procedures with use of pharmacologically allowable carriers, excipients, diluents, etc [U.S. Pat. No. 4,987,130].

According to the present invention, as compared with conventional methods, the compound (I) and an acid addition salt thereof can be produced without any step for introducing and removing protecting groups, with less reaction steps, lower production cost, short time, and higher yield. Thus, the method of this invention is remarkably advantageous from the industrial point of view. The compounds (IV) and (V) are new compounds, which are essential intermediates for the above-mentioned industrially advantageous method for the production of diethanolamine derivatives (I) or its acid addition salts.

By the following working examples, the present invention will be concretely described, but it should be understood that the invention is not limited thereto.

In working examples, room temperature means 20° to 25° C.

EXAMPLE 1

Preparation of
N,N-bis(2-hydroxyethyl)aminoacetonitrile (IV)

a) In 15 ml of methanol were dissolved 2.5 g of diethanolamine (II) and 7 ml of triethylamine. To the solution was added dropwise 3.9 g of bromoacetonitrile while stirring under cooling, then the mixture was stirred for 3 hours at room temperature. The reaction mixture was concentrated under reduced pressure. To the concentrate was added 15 ml of dichloromethane, then insolubles were filtered off. The filtrate was concentrated under reduced pressure. The concentrate was subjected to an alumina column chromatography, followed by elution with dichloromethane. Fractions containing the object compound were combined, then the solvent was distilled off under reduced pressure to leave 3.3 g (96% yield) of a colorless clear oily substance (IV).

IR(Neat)cm$^{-1}$: 3400, 2250(w).
NMR(90 MHz, DMSO—d$_6$)δ: 2.56(4H,t,J=6 Hz), 3.48(4H,t,J=6 Hz), 3.79(2H,s).

b) To 70 g of diethanolamine (II) was added dropwise 24 g of chloroacetonitrile while stirring at 50° C. or below taking one hour, then the mixture was stirring for one hour at 50° C. The reaction mixture was cooled and subjected to extraction with 200 ml of tetrahydrofuran. The oily portion of the lower layer was separated and was subjected to extraction twice with 70 ml each portions of tetrahydrofuran. Thus extracted tetrahydrofuran layers were combined and dried over anhydrous sodium sulfate and anhydrous potassium carbonate, followed by distilling off the solvent under reduced pressure to leave 45.6 g of a pale yellow clear oily substance (IV). (Apparent yield 99.6%, content 90%)

EXAMPLE 2

Preparation of
N,N-bis(n-butylcarbamoyloxyethyl)aminoacetonitrile (V')

a) In 50 ml of acetonitrile were dissolved 8 g of the compound obtained in Example 1-a) and 19 ml of triethylamine. To the solution was added 13.8 g of n-butyl isocyanate, and the mixture was stirred for 12 hours at room temperature. The reaction mixture was concentrated under reduced pressure, then the concentrate was dissolved in 200 ml of ethyl acetate and washed with 100ml of water. The resultant was washed with 100 ml of a 1N—NaOH aqueous solution and 100 ml of 1N—HCl aqueous solution and then washed with 100 ml of water and dried over anhydrous sodium sulfate. The solvent was distilled off under reduced pressure, then the residue was subjected to a silica gel column chromatography, followed by elution with dichloromethane. Fractions containing the object compound were combined, then the solvent was distilled off under reduced pressure to leave 17.1 g (90% yield) of a colorless clear oily substance (V').

IR(Neat)cm$^{-1}$: 2240(w), 1710.
NMR(90 MHz,CDCl$_3$)δ: 0.92(6 H,t,J=7 Hz), 1.10-1.96(8 H,m), 2.86(4 H,t,J=6 Hz), 3.17(4 H,t,J=6 Hz), 3.70(2 H,s), 4.17(4 H,t,J=6 Hz).

b) To 45.6 g (content 90%) of the compound (IV) obtained in Example 1-b) was added 80 g of triethylamine, and the mixture was stirred. To the mixture was added dropwise slowly 78.6 g of n-butyl isocyanate at 50° C. or below, followed by stirring for 3 hours at 50° C. The reaction mixture was concentrated under reduced pressure while distilling off triethylamine. To the residue was added 1.2 liter of isopropyl ether to make a solution. The solution was washed twice with 200 ml of a 1N-NaOH aqueous solution and twice with 200 ml of a 1N-HCl aqueous solution, followed by washing with 200 ml of water and drying over anhydrous sodium sulfate. The solvent was distilled off under reduced pressure to leave 102.5 g (apparent yield 94.6%, content 85%) of a pale yellow clear oily substance (V').

EXAMPLE 3

One-pot preparation of N,N-bis(n-butylcarbamoyloxyethyl)aminoacetonitrile (V') from diethanolamine (II)

a) In 15 ml of dichloromethane were dissolved 2.5 g of diethanolamine (II) and 6.6 ml of triethylamine. To the solution was added dropwise 4.5 g of bromoacetonitrile while stirring at 5° to 10° C. The mixture was stirred for 1.5 hour at the same temperature range, then for one hour at room temperature. To the reaction mixture was added 5.9 g of n-butyl isocyanate and the mixture was refluxed for 12 hours. To the reaction mixture were added 100 ml of dichloromethane and 50 ml of water to form two layers. The aqueous layer was re-extracted with 50 ml of dichloromethane. The dichloromethane layers were combined, washed with 50 ml of water and dried over anhydrous sodium sulfate. The solvent was distilled off under reduced pressure to leave 9.0 g (apparent yield 111%, content 69%) of a reddish brown oily substance (V').

b) In 15 ml of acetonitrile were dissolved 2.5 g of diethanolamine (II) and 6.6 ml of triethylamine. To the solution was added dropwise 4.5 g of bromoacetonitrile while stirring at temperatures ranging from 5° to 10° C. The mixture was stirred for 1.5 hour at the same temperature range, then for one hour at room temperature. To the reaction mixture was added 5.9 g of n-butyl isocyanate, and the mixture was left standing for two days at room temperature. The reaction mixture was concentrated under reduced pressure. To the concentrate were added 100 ml of dichloromethane and 50 ml of water to form two layers. The aqueous layer was re-extracted with 50 ml of dichloromethane. The dichloromethane layers were combined, washed with 50 ml of a saturated aqueous solution of sodium bicarbonate and 50 ml of water, then dried over anhydrous sodium sulfate. The solvent was distilled off under reduced pressure to leave 8.9 g (apparent yield 109%, content 75%) of a reddish brown oily substance (V').

c) In 15 ml of acetonitrile were dissolved 2.5 g of diethanolamine (II) and 6.6 ml of triethylamine. To the solution was added dropwise, while stirring at temperatures ranging from 5° to 10° C., 2.7 g of chloroacetonitrile. The mixture was stirred for 5 hours at room temperature and then left standing for 2 days at room temperature. To the reaction mixture was added 5.9 g of n-butyl isocyanate, and the mixture was stirred for 12 hours at room temperature and then left standing overnight. The reaction mixture was concentrated under reduced pressure and then to the concentrate were added 100 ml of dichloromethane and 50 ml of water to form two layers. The aqueous layer was separated and re-extracted with 50 ml of dichloromethane. The dichloromethane layers were combined, washed with 50 ml of water, then dried over anhydrous sodium sulfate. The solvent was distilled off under reduced pressure to leave 9.1 g (apparent yield 112%, content 71%) of a reddish brown oily substance (V').

EXAMPLE 4

Preparation of 2,2'-[(2aminoethyl)imino]diethanol bis(n-butylcarbamate) (I') and its dihydrochloride a) A 200 ml-capacity autoclave was charged with a solution of 9.0 g of the compound (V') obtained in Example 3-a) in 40 ml of toluene, a solution of 80 mg of sodium hydroxide in 80 ml of methanol and 3 g of Raney nickel. The reaction was allowed to proceed for 30 minutes at 80° C. under hydrogen pressure of 100 kg/cm$^2$. The reaction mixture was subjected to filtration, and the filtrate was concentrated under reduced pressure. To the concentrate was added 100 ml of dichloromethane, which was subjected to extraction with 100 ml of 1N—HCl twice. The extracted aqueous layers were combined and washed with 100 ml of ethyl acetate. The aqueous layer was made alkaline with conc. ammonia water. Resultant precipitates were subjected to extraction with 100 ml of dichloromethane. The extract was washed with 50 ml of a saturated aqueous saline solution, then dried over anhydrous sodium sulfate. The solvent was distilled off to leave about 7 g of the compound (I'). This product was dissolved in 70 ml of isopropanol, to which was added 15 ml of isopropanolic hydrogen chloride (7 mol HCl/1 liter isopropanol), and the mixture was left standing overnight. Precipitating crystals were collected under reduced pressure, washed with 50 ml of acetone, then dried at 40° C. under reduced pressure to afford 6.83 g [overall yield 68.5% from diethanolamine (II)] of dihydrochloride of the compound (I').

Elemental Analysis for $C_{16}H_{36}Cl_2N_4O_4$

Calcd. : C, 45.82; H, 8.65; N, 13.36
Found : C, 46.07; H, 8.79; N, 13.45.
IR(KBr-disc)cm$^{-1}$: 2400, 1685.
NMR(90 MHz, $D_2O$)δ: 0.86(6 H,t,J=7Hz), 1.05-1.65(8 H,m), 3.07(4 H,t,J=6.5 Hz), 3.25-3.75(8 H,m), 4.35(4 H,t,J=4.5 Hz).

b) In the same manner as in a) above, 8.9 g of the compound (V') obtained in Example 3-b) was subjected to reaction and treatment to give 7.07 g [overall yield from diethanolamine (II) — 70.9%] of dihydrochloride of the compound (I').

c) A 500 ml-capacity autoclave was charged with a solution of 20 g (content 82%) of the compound (V') obtained by the same manner as in Example 2-b) in 90 ml of toluene, a solution of 540 mg of sodium hydroxide in 180 ml of methanol and 6.7 g of Raney nickel. The reaction was allowed to proceed for 3 hours at 60° C. under hydrogen pressure of 9 kg/cm$^2$. The reaction mixture was subjected to filtration, and the filtrate was concentrated under reduced pressure. To the concentrate were added 100 ml of 1N—HCl and 100 ml of ethyl acetate. The ethyl acetate layer was separated and was re-extracted with 100 ml of 1N—HCl. The extracted aqueous layers were combined and there was added 110 ml of 1N—NaOH to make the solution alkaline (pH ca 12), then resulting precipitates were subjected to extraction with 150 ml of ethyl acetate. The ethyl acetate layer was washed with 50 ml of water, dried over anhydrous sodium sulfate, then the solvent was distilled off under reduced pressure to leave 17.1 g of the compound (I'). This product was dissolved in isopropanol, to which was added 35 ml of isopropanolic hydrogen chloride (7 mol. HCl/1 liter isopropanol), and the mixture was left standing overnight at room temperature. Crystalline precipitates were collected by filtration, washed with acetone and dried at 40° C. under reduced pressure to give 16.7 g [yield in terms of purity from the compound (V')=82.1%].

What is claimed is:

1. A compound of the formula:

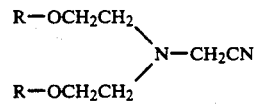

wherein R stands for a $C_{1-6}$ alkylcarbamoyl group.

2. A compound as claimed in claim 1, wherein the $C_{1-6}$ alkylcarbamoyl group is a n-butylcarbamoyl group.